(12) United States Patent
Sawyer

(10) Patent No.: US 6,500,311 B1
(45) Date of Patent: Dec. 31, 2002

(54) PROPYLENE OXIDE PURIFICATION

(75) Inventor: Gary A. Sawyer, Media, PA (US)

(73) Assignee: Arco Chemical Technology, L.P., Greenville, DE (US)

( * ) Notice: Subject to any disclaimer, the term of this patent is extended or adjusted under 35 U.S.C. 154(b) by 0 days.

(21) Appl. No.: 09/957,591

(22) Filed: Sep. 21, 2001

(51) Int. Cl.[7] .................. B01D 3/40; B01D 11/00; C07C 29/84; C07C 29/86; C07D 301/32
(52) U.S. Cl. .................. 203/44; 203/68; 203/70; 203/74; 203/76; 203/79; 549/538; 549/541; 568/913
(58) Field of Search .................. 203/43, 68, 70, 203/95, 44, 18, DIG. 23, 76, 79, 74, 14; 549/541, 538; 568/913

(56) References Cited

U.S. PATENT DOCUMENTS

| | | | |
|---|---|---|---|
| 3,843,488 A | | 10/1974 | Schmidt et al. |
| 4,824,976 A | | 4/1989 | Clerici et al. |
| 4,833,260 A | | 5/1989 | Neri et al. |
| 5,116,465 A | * | 5/1992 | Yeakey et al. .......... 203/57 |
| 5,252,758 A | | 10/1993 | Clerici et al. |
| 5,354,431 A | * | 10/1994 | Taylor .......... 203/70 |
| 5,849,938 A | * | 12/1998 | Rueter et al. .......... 549/541 |
| 6,024,840 A | * | 2/2000 | Rueter .......... 203/68 |

* cited by examiner

Primary Examiner—Virginia Manoharan
(74) Attorney, Agent, or Firm—William C. Long

(57) ABSTRACT

A mixture of propylene oxide and methanol is separated by liquid/liquid extraction using water and a hydrocarbon such as n-octane as extractive solvents.

3 Claims, 4 Drawing Sheets

PROPYLENE OXIDE PURIFICATION

BACKGROUND OF THE INVENTION

1. Field of the Invention

The present invention relates to the separation of propylene oxide and methanol by a liquid/liquid extraction process.

2. Prior Art Description

The separation or removal of methanol from propylene oxide by conventional distillation processes is difficult by reason of the low relative volatility of propylene oxide with respect to methane at higher concentrations such as concentrations above 95 wt. % or so.

Technology has been developed for the production of propylene oxide by oxidative procedures which include the use of a methanol solvent during the oxidation reaction. Illustrative of patents relating to this technology are U.S. Pat. Nos. 4,824,976, 4,833,260, 5,252,758 and the like.

Reaction mixtures produced by this technology comprise the product propylene oxide and the methanol solvent and it is important that the propylene oxide and methanol be separated as conveniently and economically as possible.

BRIEF DESCRIPTION

In accordance with the present invention, a propylene oxide and methanol solution is subjected to a liquid/liquid extraction using water and a hydrocarbon such as n-octane in order to separate the propylene oxide and methanol.

BRIEF DESCRIPTION OF THE DRAWING

The accompanying

DETAILED DESCRIPTION

Figure 1:
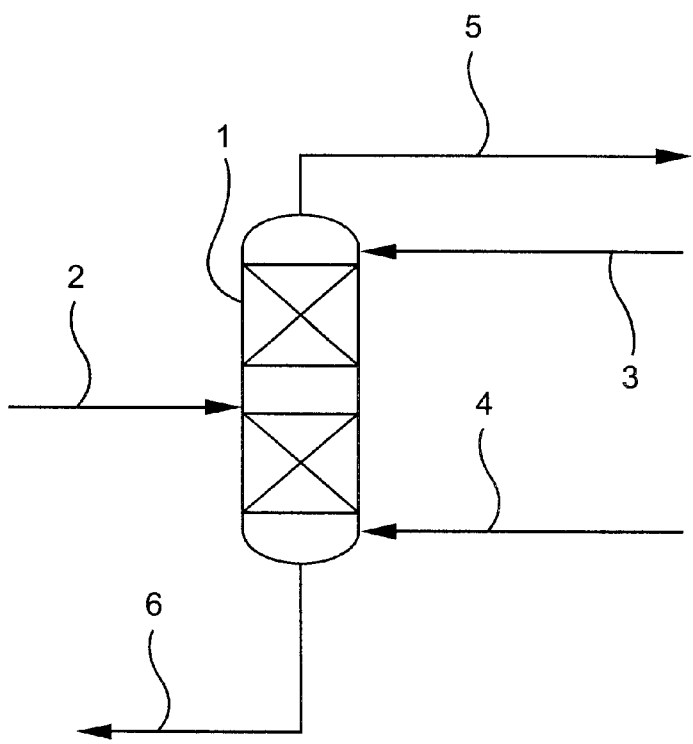
FIG. 1 provides a schematic illustration of a practice of the invention.
Figure 4:
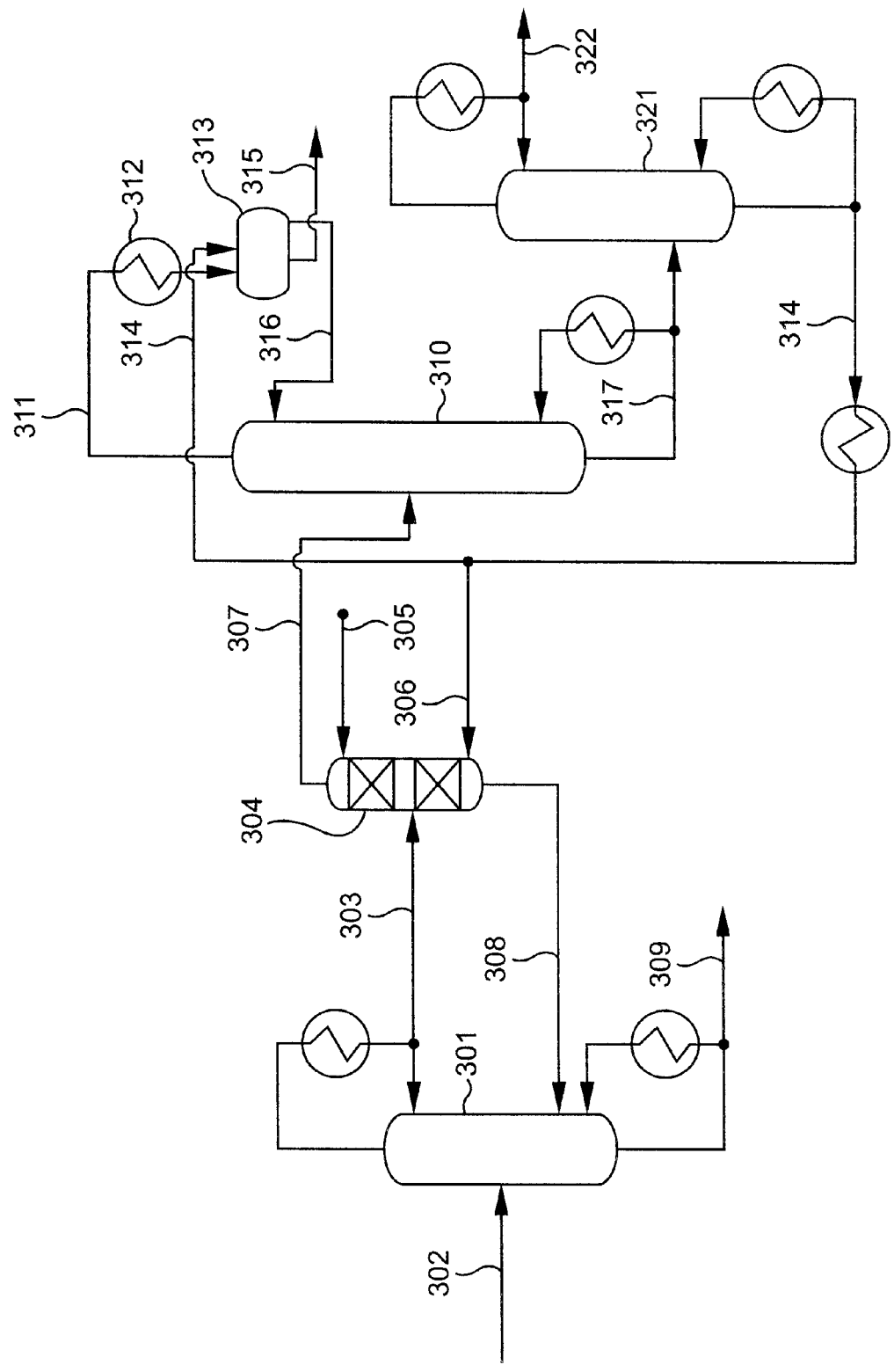

It has now been found that propylene oxide and methanol can be separated by a relatively straightforward liquid/liquid extraction procedure using as extractive solvents water and a hydrocarbon such as n-octane. In an especially preferred practice of the invention, as shown in FIG. 1, a liquid stream comprised of propylene oxide and methanol is fed to a conventional continuous extraction column 1 via line 2. Water as an extractive solvent is fed to the column at the upper end via line 3, and a hydrocarbon such as n-octane is fed to the column at the lower end via line 4. In the extraction column, water flows downwardly extracting with it methanol contained in the feed. The hydrocarbon, on the other hand, flows upwardly through the column carrying with it propylene oxide. Thus, from the column an upper liquid stream is recovered via line 5 comprised of the hydrocarbon solvent and the extracted propylene oxide substantially reduced in methanol, while from the bottom of the column an aqueous stream, comprised of the extractive water solvent and methanol is removed via line 6. The removed streams can be suitably processed in a conventional manner to recover the components. Thus, the hydrocarbon extractive solvent and propylene oxide stream can be fractionated to separate the hydrocarbon which can be conveniently reused in the extraction step. The separated propylene oxide can be further purified by conventional methods in order to obtain a suitably high purity product propylene oxide. In processes where high purity propylene oxide is accomplished with extractive distillation, the hydrocarbon extractive solvent stream 5 can be fed directly to extractive distillation, making this invention particularly convenient for removal of methanol as shown in FIG. 4. As to the aqueous stream, this stream can be treated by conventional distillation to separate methanol and water. Methanol can conveniently returned to the propylene oxide forming reaction where it functions as an effective solvent, and water can be recycled to the extraction.

In carrying out the present invention, no special conditions of temperature or pressure are necessary for successful separation of propylene oxide and the methanol. Generally speaking temperatures ranging from about 60 to 150° F. or are suitable and pressures close to normal can be employed.

The feed streams, which are treated in accordance with the present invention, are comprised of propylene oxide and methanol, preferably from a catalyzed hydrogen peroxide oxidation of propylene. Generally it is advisable to subject the feed first to a distillation, especially where methanol concentrations are high, in order to remove methanol before extraction. The feed to the extraction process generally will comprise by weight about 2 to 10% methanol with the remainder essentially propylene oxide.

The extractive hydrocarbon solvent employed accordingly to the present invention is a saturated hydrocarbon, preferably a $C_7$–$C_9$ saturated paraffin hydrocarbon. Octane is preferred because it is not only an effective extraction solvent but frequently in propylene oxide purification procedures n-octane is employed in an extractive distillation whereby trace impurities are removed from propylene oxide. Other saturated hydrocarbons which are useful include n-heptane and n-nonane as well as branched saturated hydrocarbons having 7–9 carbon atoms.

Through practice of the present invention, the separation of methanol from propylene oxide is effectively accomplished. Purities of product propylene oxide with respect to contained methanol achieved through practice of the invention can range from about 99.8 to 99.995 wt. % purity usually 99.9 to 99.95 wt. % purity.

Then invention is especially suitable in conjunction with procedures for the manufacture of propylene oxide which involve the oxidation of propylene with hydrogen peroxide carried out in the liquid phase using a methanol containing solvent. The mixtures, which are resolved in accordance with the invention can be mixtures of propylene oxide and methanol as well as propylene oxide and methanol plus water.

In general, commercially available propylene oxide has a purity in excess of 99.95%. Oxygenated hydrocarbons such as acetaldehyde, methanol, and methyl formate are key impurities, along with water and hydrocarbons such as hexenes and hexanes. Several refining schemes are possible to provide propylene oxide at these low impurity levels, including extractive distillation with heavy hydrocarbons such as octanes.

Figure 2:
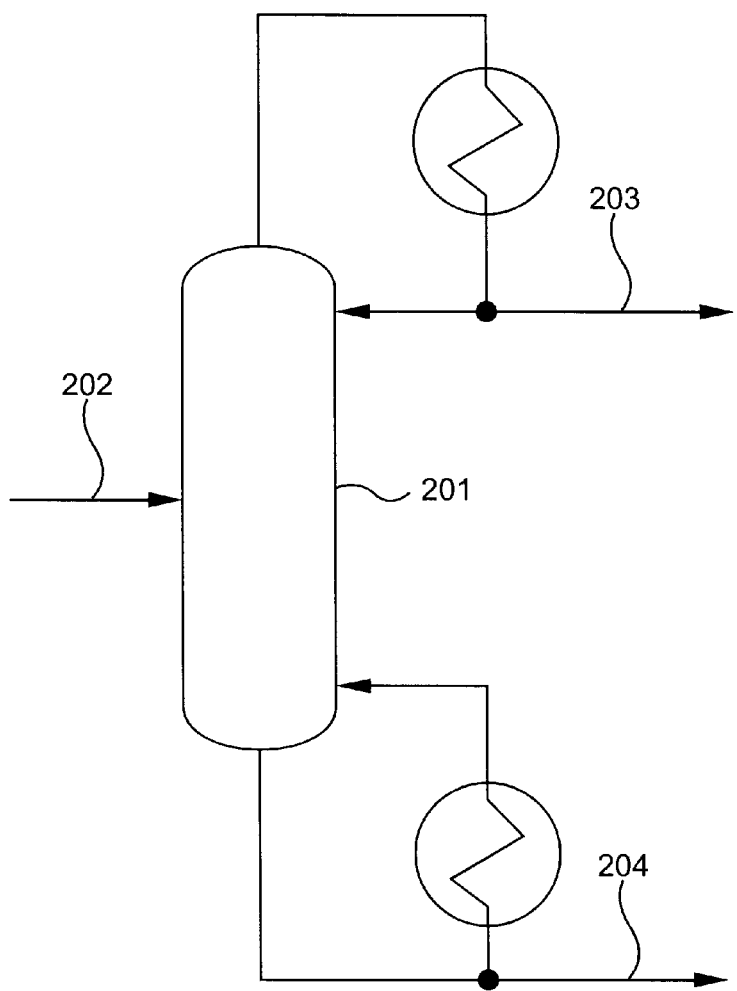
FIG. 2 provides a schematic illustration of a comparative process not according to the invention.

For example, FIG. 2 illustrates for comparative purposes a simple distillation to obtain crude propylene oxide with methanol concentrations typical of those encountered in the feed to a commercial propylene oxide refining operation.

The propylene oxide reaction mixture which typically may comprise 10 wt. % propylene oxide, 5 wt. % water and 85 wt. % methanol and impurities is introduced in to distillation column 201 via line 202 and fractionally distilled to recover overhead via line 203 a propylene oxide stream of 99+% propylene oxide which is suitable as feed to a commercial propylene oxide refining operation. The methanol and water bottoms stream is separated via line 204.

A disadvantage of such a straight distillation procedure is that a large distillation column having many theoretical stages is required along with high reflux ratios in order to achieve the appropriate separation.

It is possible to economically do a rough distillation of the propylene oxide reaction mixture to substantially concentrate propylene oxide and in an especially advantageous practice of the invention such a rough distillation is performed prior to the liquid/liquid extraction according to the invention. Such a procedure is illustrated in FIG. 3.

Figure 3:
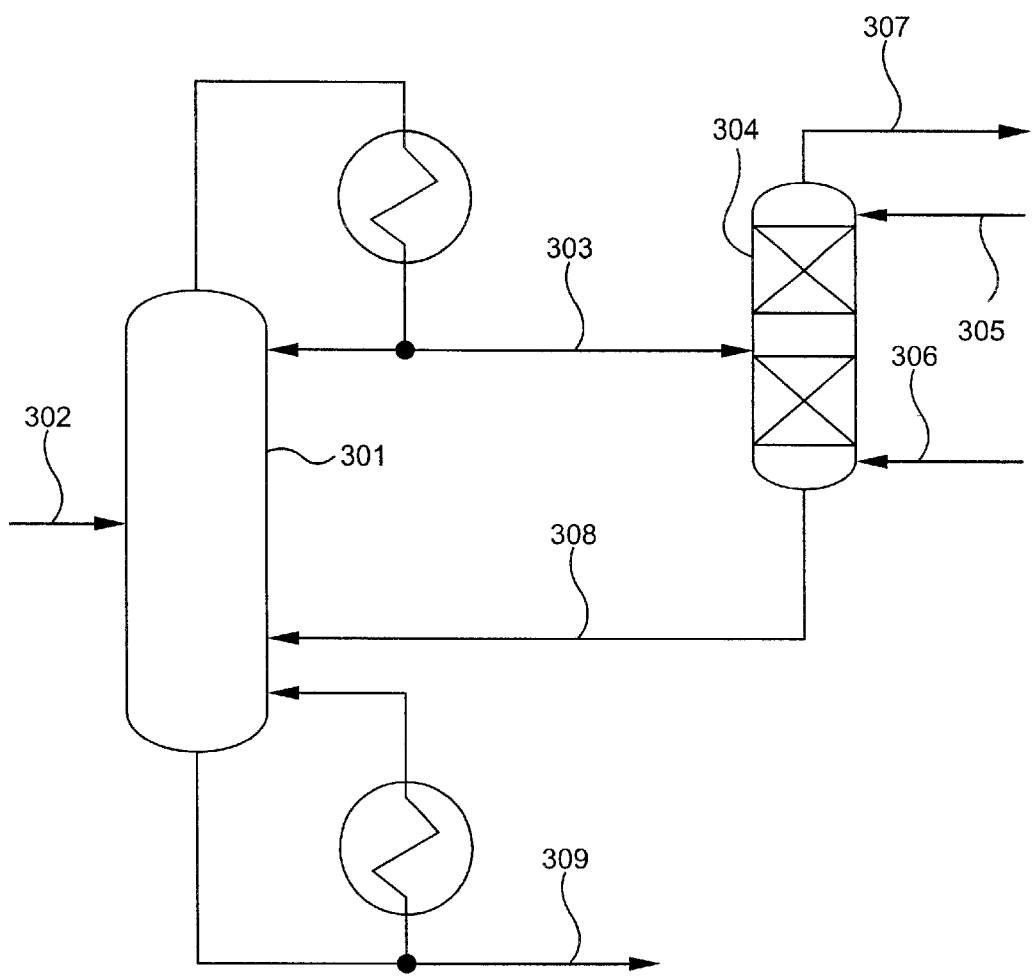
FIGS. 3 and 4 show schematic illustrations of preferred practices of the invention.

With reference to FIG. 3, a propylene oxide reaction mixture such as described above in connection with FIG. 2 is introduced to distillation column 301 via line 302 and therein fractionally distilled to recover an overhead rough crude propylene oxide which is greatly concentrated in propylene oxide with respect to the feed, for example 95 wt. % propylene oxide and 5 wt. % methanol and impurities, and which is removed via line 303.

Far fewer theoretical stages and lower reflux ratios can be employed in column 301 as compared to those needed for the separation in column 201 previously described.

The rough crude propylene oxide stream passes via line 303 to liquid/liquid extractor 304 to which is introduced water extractant via line 305 and octane extractant via line 306. The liquid/liquid extraction is carried out as described in connection with FIG. 1, the octane and propylene oxide stream being removed via line 307 and the water methanol stream being removed via line 308.

Conveniently the water and methanol stream passes back to column 301 via line 308 as shown and from column 301 a methanol and water stream is recovered via line 309.

By the distillation and extraction sequence shown in FIG. 3 it is possible to obtain a propylene oxide stream via line 307 which is comparable to that obtained via line 203 of FIG. 2 in a much more economic manner.

In certain processes propylene oxide is refined to commercially acceptable purities by extractive distillation using an extractive solvent such as octane. See, for example, U.S. Pat. No. 3,843,488.

FIG. 4 illustrates especially preferred practice of the invention which integrates the liquid/liquid extraction with extractive distillation using octane solvent.

Referring to FIG. 4, the octane and propylene oxide extraction stream passes from extractor 304 via line 307 to extractive distillation column 310 wherein methanol, water and light impurities are separated as overhead vapor along with some octane via line 311. The overhead is condensed in condenser 312 and passed to decanter 313 along with liquid octane via line 314. An aqueous purge with methanol and light impurities is separated via line 315. Octane is returned as reflux via line 316 to column 310.

From column 310 a bottoms octane and propylene oxide stream is removed via line 317 to column 321 wherein refined propylene oxide of high purity is recovered via line 322. Octane is passed via line 314 to decanter 313 with a portion passing via line 306 to extractor 304.

It is worth noting that if the rough crude propylene oxide from column 301 is passed to extractive distillation without the liquid/liquid extraction step, the methanol and light impurities can be removed in an aqueous stream from the overhead decanter. However, the methanol cannot be conveniently be recycled since there is no outlet for the light impurities.

As above described, the process of the invention is especially useful in separating propylene oxide and methanol such are present in the reaction mixtures resulting from the reaction of propylene and hydrogen peroxide using a methanol solvent.

EXAMPLE

Referring to FIG. 4, the reaction mixture from the catalytic reaction of hydrogen peroxide and propylene in methanol solvent to form propylene oxide is fed via line 302 to distillation column 301 wherein a crude separation of methanol and propylene oxide takes place. An overhead crude propylene oxide stream is removed and passes via line 303 to extraction column 304 wherein it is subjected to the liquid/liquid extraction in accordance with the invention.

Column 304 is a conventional extractor adapted to provide intimate contact of the various liquid streams fed thereto. The water extraction solvent is fed to column 304 via line 305 near the upper end and n-octane extraction solvent is fed via line 306 near the lower end. The water extraction solvent passes downwardly through the column and is removed together with extracted methanol via line 308 and conveniently passed, as shown, to column 301 for separation of minor amounts of n-octane contained therein. An aqueous methanol stream is recovered from column 301 via line 309 and this stream can be treated by conventional means for recovery of methanol which can be reused in the propylene reaction to form propylene oxide.

The n-octane extraction solvent stream containing extracted propylene oxide is recovered from column 304 via line 307 and passes to distillation column 310 wherein light impurities are separated by extractive distillation. Overhead from column 310 passes va line 311 to condenser 312 and decanter 313 and n-octane is fed to decanter 313 via line 314. A small purge stream is removed from decanter 313 via line 315. Reflux n-octane passes via line 316 to column 310 and a bottoms stream is removed therefrom via line 317 and passed to distillation column 321. A propylene oxide product stream from which the great bulk of the methanol has been separated is recovered overhead via line 322, and a bottoms n-octane stream is recovered via line 314.

The accompanying table is provided which gives the flow rates, compositions, and conditions at the various points in the process described above. It can be seen that practice of the invention provides essentially complete separation of methanol from the propylene oxide in an economic and convenient procedure.

TABLE

| Steam ID | 302 | 303 | 305 | 306 | 307 | 308 | 309 |
|---|---|---|---|---|---|---|---|
| Temperature F. | 110 | 111.2 | 110 | 120 | 109.6 | 118.3 | 187 |
| Pressure, PSI | 200 | 20 | 100 | 100 | 30 | 30 | 29.6 |
| Vapor Frac | 0 | 0 | 0 | 0 | 0 | 0 | 0 |
| Mole Flow, LBMOL/HR | 23405 | 1430 | 1493 | 1751 | 3143 | 1531 | 23505 |
| Mass Flow LB/HR | 752771 | 79803 | 26897 | 200000 | 277394 | 29306 | 702274 |

TABLE-continued

| Mass Flow LB/HR | | | | | | | |
|---|---|---|---|---|---|---|---|
| Propylene Oxide | 75861 | 75786 | 0 | 0 | 75785 | 1 | 76 |
| Methanol | 636865 | 3990 | 0 | 0 | 76 | 3914 | 636789 |
| Water | 40045 | 16 | 26897 | 0 | 1539 | 25374 | 65403 |
| Normal Octane | 0 | 11 | 0 | 200000 | 199994 | 16 | 6 |
| Mass Frac | | | | | | | |
| Propylene Oxide | 0.1010 | 0.9500 | 0.0000 | 0.0000 | 0.2730 | 0.0000 | 0.0000 |
| Methanol | 0.8460 | 0.0500 | 0.0000 | 0.0000 | 0.0000 | 0.1340 | 0.9070 |
| Water | 0.0530 | 0.0000 | 1.0000 | 0.0000 | 0.0060 | 0.8660 | 0.0930 |
| Normal Octane | 0.0000 | 0.0000 | 0.0000 | 1.0000 | 0.7210 | 0.0010 | 0.0000 |
| Steam ID | 311 | 313 | 314 | 315 | 316 | 319 | 322 |
| Temperature F. | 168.6 | 120 | 316.9 | 100 | 100 | 216.4 | 122.4 |
| Pressure, PSI | 30 | 80 | 33.6 | 30 | 30 | 42.6 | 25 |
| Vapor Frac | 1 | 0 | 0 | 0 | 0 | 0 | 0 |
| Mole Flow, LBMOL/HR | 549 | 2626 | 4377 | 90 | 3085 | 5680 | 1303 |
| Mass Flow LB/HR | 30000 | 300000 | 499995 | 1738 | 328262 | 575657 | 75662 |
| Mass Flow LB/HR | | | | | | | |
| Propylene Oxide | 22771 | 0 | 1 | 123 | 22648 | 75662 | 75660 |
| Methanol | 421 | 0 | 0 | 76 | 345 | 0 | 0 |
| Water | 1794 | 0 | 0 | 1538 | 256 | 1 | 1 |
| Normal Octane | 5013 | 300000 | 500000 | 0 | 305013 | 500000 | 0 |
| Mass Frac | | | | | | | |
| Propylene Oxide | 0.7590 | 0.0000 | 0.0000 | 0.0710 | 0.0690 | 0.1310 | 1.0000 |
| Methanol | 0.0140 | 0.0000 | 0.0000 | 0.0440 | 0.0010 | 0.0000 | 0.0000 |
| Water | 0.0600 | 0.0000 | 0.0000 | 0.8850 | 0.0010 | 0.0000 | 0.0000 |
| Normal Octane | 0.1670 | 1.0000 | 1.0000 | 0.0000 | 0.9290 | 0.8690 | 0.0000 |

I claim:

1. A process for the separation of a mixture of propylene oxide and methanol comprising fractionally distilling a mixture comprised of propylene oxide and methanol, recovering a distillate mixture comprised of propylene oxide and methanol which is concentrated in propylene oxide, contacting the mixture which is concentrated in propylene oxide with water and $C_7$–$C_9$ hydrocarbon extractive solvents in a liquid/liquid solvent extraction and separately recovering a stream comprised of the aqueous extractive solvent and methanol and a stream comprised of the extractive hydrocarbon solvent and propylene oxide.

2. The process of claim 1 wherein the hydrocarbon extractive solvent is octane.

3. The process of claim 1 wherein extracted propylene oxide and hydrocarbon solvent is subjected to an extractive distillation.

* * * * *